(12) United States Patent
Suhonen et al.

(10) Patent No.: US 6,289,904 B1
(45) Date of Patent: Sep. 18, 2001

(54) DENTAL FLOSS

(75) Inventors: Christopher Suhonen, Alto, MI (US); Jose E. Fontana, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/581,113

(22) PCT Filed: Dec. 9, 1998

(86) PCT No.: PCT/US98/26150

§ 371 Date: Aug. 15, 2000

§ 102(e) Date: Aug. 15, 2000

(87) PCT Pub. No.: WO99/29257

PCT Pub. Date: Jun. 17, 1999

Related U.S. Application Data

(60) Provisional application No. 60/069,187, filed on Dec. 10, 1997.

(51) Int. Cl.$^7$ .................................................. A61C 15/00
(52) U.S. Cl. ............................................................ 132/321
(58) Field of Search ............................................. 132/321

(56) References Cited

U.S. PATENT DOCUMENTS

| | | | |
|---|---|---|---|
| 4,996,056 | * | 2/1991 | Blass ................................. 132/321 X |
| 5,033,488 | | 7/1991 | Curtis et al. . |
| 5,209,251 | | 5/1993 | Curtis et al. . |
| 5,842,489 | * | 12/1998 | Suhonen et al. ...................... 132/321 |

FOREIGN PATENT DOCUMENTS

| | | | |
|---|---|---|---|
| 0 423 541 B1 | | 4/1995 | (EP) . |
| WO91 08792 | * | 6/1991 | (WO) . |
| WO93 02633 | * | 2/1993 | (WO) . |

* cited by examiner

*Primary Examiner*—Nicholas D. Lucchesi
(74) *Attorney, Agent, or Firm*—Michael J. McGreal

(57) ABSTRACT

The nylon fiber strand is coated with a coating to produce a coated surface on the nylon that mimics the surface characteristics of polytetrafluoroethylene (PTFE). The coating is comprised of a base prime coat and a top finish coat. These coatings are applied separately to the nylon fiber strand. The top finish coat which is also known as the nylon wax coat is comprised of waxes, an ester and a silicone, and primarily of waxes. The waxes are comprised of a mixture of a low melting point wax and a high melting point wax.

14 Claims, No Drawings

DENTAL FLOSS

This application is a 371 of PCT/US98/26150 filed Dec. 9, 1998, which claims benefit of Prov. No. 60/069,187 filed Dec. 10, 1997.

FIELD OF THE INVENTION

This invention relates to a dental floss that can be readily gripped and which can be readily inserted into close interdental spaces. More particularly, this invention relates to a tape type of dental floss that has a coating that increases the lubricity of the base fiber to make it easier to use.

BACKGROUND OF THE INVENTION

A well-recognized problem with regard to flosses, whether they are tape flosses or multifilament flosses, is the catching on tooth surfaces during movement into and through close contact interdental spaces. In some instances the floss will break and shred and parts of the floss will become stuck between the teeth. It then takes more flossing to remove floss segments from between one's teeth. This has been a continuing problem which is solved through the use of the new polytetrafluoroethylene (PTFE) fiber flosses. However, PTFE is a relatively expensive fiber. Therefore, it has been an objective to provide a fiber that has the ease of use characteristics of PTFE while using a lower cost fiber. This can be the result of forming a particular fiber composition or it can be by providing a coating on a non-PTFE fiber that makes the non-PTFE fiber mimic a PTFE fiber in use as a floss. Since a PTFE fiber has a low coefficient of friction (COF), it inherently readily passes into close interdental spaces.

PTFE flosses are disclosed in U.S. Pat. Nos. 5,033,488 and 5,209,251. These consist of one or more strands of expanded PTFE with a wax or other coating to increase the grippability of the fiber in use as a floss. A microcrystalline wax was found to be one effective wax. However, other coatings that adhere to PTFE, that are not brittle at about room temperature and which have a melting point above 50° C. can be used. The coating will raise the COF of the expanded PTFE above about 0.08. A wax coated non-PTFE fiber floss is disclosed in U.S. Pat. No. 4,996,056. In this patent there is disclosed a nylon, polyester or polypropylene fiber that is coated with solid particles of a fluoropolymer in a binder. The binder can be a wax or a non-wax, with a wax being preferred. The fluoropolymer particles can be PTFE particles of a particle size of about 1 to 50 millimicrons. European Patent Application 423 541 A2 discloses formulations for coating flavorants and other materials onto PTFE surfaces, including flosses.

These patent publications set out the present state of the art of flosses that contain PTFE. The expanded PTFE fiber flosses slip easily into tight interdental spaces. However, expanded PTFE film can cost 3 to 10 times the cost of other fibers. Although a useful floss fiber, it is expensive. The non-PTFE fiber coated with particulate PTFE is not a low COF floss. This is the case since the PTFE particle coating is scrapped from the fiber during insertion between the teeth and the subsequent motion of the floss. The full benefits of a PTFE fiber then are no longer achieved.

Waxes have been coated onto conventional floss fibers for many years. Although microcrystalne waxes are the most commonly used waxes, other waxes, such as beeswax, paraffin waxes, carnauba wax and polyethylene wax can also be used. The floss fibers are usually nylon, however, other fibers such as polyethylene, polypropylene, polyester, cellulose and cotton also are used. The wax coating lubricates the fiber so that it can more easily slip into tight interdental spaces and also serves as a binder for multifilament flosses. However, none of these coatings onto these floss fibers have proven to impart to the non-PTFE fibers the characteristics of PTFE flosses. The objective is to use a lower cost conventional fiber and to achieve the surface lubricity of PTFE.

BRIEF SUMMARY OF THE INVENTION

It has been found that non-PTFE fibers such as nylons, polyenes such as polyethylene, polypropylene and polybutadiene, polyesters, ethylene-propylene copolymers, ethylene-vinyl acetate copolymers, ethylene vinyl alcohol copolymers, and cellulosics can be coated so that they can gain at least some of the surface characteristics similar to those of PTFE. The usual PTFE flosses are in the form of a tape. They usually are of about 800 to 1500 denier prior to any coating. A non-PTFE fiber strand can be made to mimic many of the surface characteristics of PTFE by the application of a two-stage coating. The non-PTFE fiber strand is first coated with a nylon bonding coating and then with a wax coating. The nylon bonding coat is in the nature of a primer coat. The wax coat is the coating which is to duplicate as much as possible the desirable properties of PTFE. The overall coating level of the two coatings onto the fiber strand is about 12% to 22% by weight. The ratio of the wax coating to the nylon bonding coating is about 1:1 to about 3:1.

The two-stage coating process produces a non-PTFE fiber strand that has the lubricious surface characteristics of PTFE. The strand slips readily between teeth, including teeth with tight interdental spaces. The coated strand also is easy to grip for flossing. The fiber strand does not slip from between a person's fingers when the strand gets caught between two closely spaced teeth.

DETAILED DESCRIPTION OF THE INVENTION

It has been found that a non-PTFE fiber strand can be produced that has surface characteristics similar to many of those of PTFE. That is, it has a lubricious surface that mimics the surface of PTFE in use as a floss. A preferred film strand is nylon and the invention will be described with regard to nylon but with the understanding that other films will be used.

The nylon fiber strand can be a monofilament strand or a multifilament strand. It will have a denier of about 300 to 2000 denier. The nylon bonding coat is comprised of a polyamide solution, a silicone, PTFE resin powder and an alcohol as the solubilizing and application vehicle. The formulation contains about 10% to about 20% of the polyamide solution, and preferably about 15% by weight. The silicone is present in an amount of about 0.5% to about 3% by weight, and preferably about 1.5%. The PTFE resin powder is present in an amount of about 0.2% to about 1% by weight, and preferably about 0.5%. The remainder is alcohol carrier and solubilizing vehicle which alcohol usually is ethanol.

The wax coat is comprised of waxes, along with glycerol esters and silicones. Preferably the waxes are comprised of a mixture of a low melting point wax and a high melting point wax. A low melting point wax is a wax that has a melting point between about 50° C. and 65° C. A high melting point wax is a wax that has a melting point above about 75° C. The coating also includes a glycerol ester, such as glycerol triacetate, and a silicone.

The silicone preferably is a silicone copolymer. The silicone provides the formulation which creates a silky, slippery surface effect on the fiber surface. Suitable silicone copolymers are organosilicones.

The waxes comprise about 80% to about 96% by weight of the formulation. The low melting point wax is present in a ratio of about 1:1 to about 2:1 of the high melting point wax. The glycerol ester is present in an amount of about 5% to about 10% by weight with the silicone being present in an amount of 1% to 3% by weight. The preferred glycerol ester is glycerol triacetate. The preferred silicone is a silicone copolymer such as methylalkyl polysiloxane copolymer.

The nylon bond coating is put into the nylon in a first step. This can be put onto the nylon strand using essentially any coating technique. These include lick roll, submersion and squeeze rolls and spraying. After coating, the fiber strand is heated to remove the ethanol. The fiber strand then is coated with the wax coat. This wax coat can be put onto the fiber by any of the above mentioned techniques.

The overall coating level on the fiber strand is about 12% to about 22% by weight. The ratio of the wax coating to the nylon bond coating is about 1:1 to about 3:1.

EXAMPLE 1

A nylon fiber having a nominal 700 denier was coated with the nylon bonding coat and the wax coat. The nylon bonding coat is applied at a coating of 6.5 percent by weight and the wax coat is applied at a coating of 11 percent by weight at a total coating level of 17.5%. The coating is applied by immersing the fiber into a bath containing the coating with the excess removed by a squeegee.

The coatings have the following compositions:

| Nylon Bonding Coating | |
|---|---|
| Polyamide Stock Solution | 15% by weight |
| Dimethicone Copolyol | 1.5% by weight |
| PTFE Resin Powder | 0.5% by weight |
| Ethanol | 83.0% by weight |
| Wax Coating | |
| Low-melting Point Wax | 53% by weight |
| Beeswax | 38% by weight |
| Glycerol Triacetate | 7% by weight |
| Silicone Copolymer | 2% by weight |

The coated nylon fiber has a denier of 873 and a break strength of 45 Newtons. The relative friction is greater than PTFE flosses but less than commercially available wax coated nylon fibers.

What is claimed is:

1. A dental floss comprising a non-PTFE fiber having a denier of about 300 to 2000 and coated with a first coating and a second coating, said second coating overlaying said first coating, said first coating being a nylon bonding coating comprising primarily a polyamide dispersed in an alcohol carrier for application to said non-PTFE fiber and said second coating being primarily a wax coating.

2. A dental floss as in claim 1 wherein said first coating is comprised of a polyamide solution, a silicone and PTFE resin powder in an alcohol solubilizing vehicle.

3. A dental floss as in claim 2 wherein said polyamide is present in about 10% to about 20% of the polyamide solution by weight, the silicone is present in about 0.5% to about 3% by weight, the PTFE resin powder is present in an amount of about 0.2% to about 1% by weight, the remainder being said alcohol solubilizing vehicle.

4. A dental floss as in claim 3 wherein said wax coating contains at least one glycerol ester and at least one silicone.

5. A dental floss as in claim 4 wherein said wax is a mixture of a first wax having a melting point of between about 50° C. and about 65° C. and a second wax having a melting point of more than about 75° C.

6. A dental floss as in claim 5 wherein said first wax is present in a ratio of about 1:1 to about 2:1 of said second wax.

7. A dental floss as in claim 4 wherein said wax comprises about 80% to about 96% by weight of said second coating.

8. A dental floss as in claim 7 wherein said glycerol ester is present in an amount of about 5% to about 10% by weight of said second coating.

9. A dental floss as in claim 8 wherein said silicone is present in an amount of about 1% to about 3% by weight of said second coating.

10. A dental floss as in claim 4 wherein said wax is selected from the group consisting of microcrystalline waxes, beeswax, paraffin waxes, carnauba wax and polyethylene waxes.

11. A dental floss as in claim 1 wherein the ratio of said first coating to said second coating is about 1:1 to about 3:1.

12. A dental floss as in claim 1 wherein the coating of said first coating and said second coating on said non-PTFE fiber is about 12% to about 22% by weight of said floss.

13. A dental floss as in claim 1 wherein said non-PTFE fiber is selected for the group consisting of nylons, polyenes polyesters, ethylene-propylene copolymers, ethylene-vinyl acetate copolymers, ethylene vinyl alcohol copolymers and cellulosics.

14. A dental floss as in claim 13 wherein said non-PTFE fiber is a nylon.

* * * * *